(12) United States Patent
Gerber et al.

(10) Patent No.: US 7,604,629 B2
(45) Date of Patent: Oct. 20, 2009

(54) MULTI-PARAMETER INFECTION MONITORING

(75) Inventors: Martin T. Gerber, Maple Grove, MN (US); John C. Rondoni, Plymouth, MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 11/737,181

(22) Filed: Apr. 19, 2007

(65) Prior Publication Data
US 2008/0262323 A1    Oct. 23, 2008

(51) Int. Cl.
*A61K 9/22* (2006.01)
(52) U.S. Cl. ................................. 604/891.1
(58) Field of Classification Search .......... 604/65, 604/31, 502, 503–505, 66, 67, 890.1, 891.1; 600/549, 300; 607/6
See application file for complete search history.

(56) References Cited

U.S. PATENT DOCUMENTS

| | | | |
|---|---|---|---|
| 5,029,582 A | 7/1991 | Lekholm | |
| 5,181,905 A | 1/1993 | Flam | |
| 5,546,955 A | 8/1996 | Wilk | |
| 5,807,270 A | 9/1998 | Williams | |
| 5,820,263 A | 10/1998 | Ciobanu | |
| 6,113,539 A | 9/2000 | Ridenour | |
| 6,135,968 A | 10/2000 | Brounstein | |
| 6,248,080 B1 * | 6/2001 | Miesel et al. | 600/561 |
| 6,282,444 B1 | 8/2001 | Kroll | |
| 6,356,774 B1 | 3/2002 | Bernstein | |
| 6,558,351 B1 | 5/2003 | Steil | |
| 6,963,772 B2 | 11/2005 | Bloom | |
| 6,970,741 B1 | 11/2005 | Whitehurst | |
| 7,049,824 B2 | 5/2006 | Shabino | |
| 2002/0042596 A1 | 4/2002 | Hartlaub | |
| 2003/0032892 A1 | 2/2003 | Erlach | |
| 2003/0199783 A1 | 10/2003 | Bloom | |
| 2003/0216677 A1 | 11/2003 | Pan | |
| 2004/0066313 A1 * | 4/2004 | Ong et al. | 340/870.11 |
| 2005/0012610 A1 | 1/2005 | Liao | |
| 2005/0090761 A1 | 4/2005 | Carney | |
| 2005/0096584 A1 | 5/2005 | Ferek-Petric | |
| 2006/0062852 A1 | 3/2006 | Holmes | |
| 2006/0079793 A1 | 4/2006 | Mann | |
| 2006/0149331 A1 | 7/2006 | Mann | |
| 2006/0224088 A1 | 10/2006 | Roche | |
| 2006/0271108 A1 | 11/2006 | Libbus | |

(Continued)

FOREIGN PATENT DOCUMENTS

DE     10150343 A1     4/2003

(Continued)

OTHER PUBLICATIONS

U.S. Appl. No. 60/825,101, filed Sep. 2006, Lee et al.*

(Continued)

*Primary Examiner*—Loan H. Thanh
*Assistant Examiner*—Deanna K Hall
(74) *Attorney, Agent, or Firm*—Campbell Nelson Whipps LLC

(57) ABSTRACT

Methods for monitoring an infection in proximity to an implantable medical device include monitoring a first indicator of infection in proximity to a medical device implanted in a patient; monitoring a second patient parameter; and determining whether the combination of the first indicator and the second parameter are indicative of infection in proximity to the implanted device. If a determination is made that the combination of the first indicator and the second parameter are indicative of infection, an alert may be issued.

12 Claims, 11 Drawing Sheets

U.S. PATENT DOCUMENTS

2008/0064980 A1* 3/2008 Lee et al. .................. 600/547

FOREIGN PATENT DOCUMENTS

| GB | 2 405 203 | 2/2005 |
|----|-----------|--------|
| WO | WO 02/068049 | 9/2002 |
| WO | WO 2005/000091 | 1/2005 |
| WO | WO 2005/000160 | 1/2005 |
| WO | WO 2006/013585 | 2/2006 |
| WO | WO 2006/048554 | 5/2006 |
| WO | WO 2007/028035 | 3/2007 |

OTHER PUBLICATIONS

U.S. Appl. No. 11/737,180, filed Apr. 19, 2007, Gerber.
U.S. Appl. No. 11/737,173, filed Apr. 19, 2007, Gerber.
U.S. Appl. No. 11/737,176, filed Apr. 19, 2007, Gerber.
U.S. Appl. No. 11/737,179, filed Apr. 19, 2007, Gerber.
U.S. Appl. No. 11/737,171, filed Apr. 19, 2007, Gerber.
U.S. Appl. No. 11/737,170, filed Apr. 19, 2007, Gerber.
U.S. Appl. No. 11/737,169, filed Apr. 19, 2007, Gerber.
Robicsek, F., et al., The value of thermography in the early diagnosis of postoperative sternal wound infections. Thoracic & Cardiovascular Surgeon, 1984. 32(4): p. 260-5.
Saxena, A.K., et al., Thermography of Clostridium perfringens infection in childhood, Pediatric Surgery International, 1999. 15(1): p. 75-6.
Waterman, N.G., L. Goldberg, and T. Appel, Tissue temperatures in localized pyogenic infections. American Journal of Surgery, 1969. 118(1): p. 31-5.
PCT International Search Report dated Oct. 10, 2007.
PCT International Search Report dated Nov. 19, 2007.
PCT International Search Report dated Dec. 5, 2007.

* cited by examiner

MULTI-PARAMETER INFECTION MONITORING

Field

This disclosure relates, *inter alia*, to implantable medical devices. More particularly, it relates to systems, devices and methods for monitoring infection in proximity to medical devices implanted in patients.

BACKGROUND

Infection associated with implantation of medical devices is a serious health and economic concern. Today, infections associated with implanted medical devices are not very common due to care and precautions taken during surgical implantation of the devices. However, when infection associated with an implanted medical device (IMD) does occur, explanting the device is often the only appropriate course of action.

For IMDs having a battery powered component, such as implantable cardiac pacemakers, cardioverter/defibrillators having pacing capabilities, other electrical stimulators including spinal cord, deep brain, nerve, and muscle stimulators, infusion devices, cardiac and other physiologic monitors, cochlear implants, etc., the battery powered component is typically enclosed in a housing that is implanted subcutaneously at a surgically prepared site, referred to as a "pocket". Associated devices, such as elongated medical electrical leads or drug delivery catheters, extend from the pocket to other subcutaneous sites or deeper into the body to organs or other implantation sites.

Surgical preparation and implantation are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections do occur. In addition, once the pocket becomes infected, the infection can migrate along the lead or catheter to the heart, brain, and spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Accordingly, aggressive systemic drug treatment is prescribed to treat such infections. However, early detection of infection associated with implanted medical devices may allow for earlier intervention, resulting in fewer device explants.

Monitoring of infection through the use of sensors, such as temperature and pH sensors that can provide information indicative of infection, has been proposed. However, because a given variable measured in proximity to an implantable medical device may vary for reasons other than the presence of an infection, it may be difficult to accurately determine whether such individually sensed indicators are indicative of an infection.

SUMMARY

The present disclosure describes, *inter alia*, systems, devices and methods that can be used to monitor an infection in proximity to an implanted medical device by monitoring two or more parameters. By taking into account more than one variable, the accuracy of a determination based on sensed information as to whether an infection is present in proximity to an implanted medical device may be improved.

In various embodiments, a method for monitoring infection in proximity to an implanted medical device is described. The method includes monitoring a first indicator of infection in proximity to a medical device implanted in a patient and monitoring a second patient parameter. The method further includes determining whether the combination of the first indicator and the second parameter are indicative of infection in proximity to the implanted device. The determination as to whether the combination of the first indicator and the second parameter are indicative of infection may be made by determining whether a value associated with the first indicator crosses a threshold and whether a value associated with the second patient parameter crosses a threshold. Monitoring of the second patient parameter may begin, or increase in frequency, after it is determined whether the value associated with the indicator of infection has crossed a threshold.

By providing devices, systems and methods that take into account more than one patient parameter when determining whether an infection is present in proximity to an implanted medical device, the accuracy of such determinations may be improved. For example, increased temperature in proximity to an implanted medical device may be indicative of infection, but may also be indicative of increased patient activity. By comparing patient activity to temperature in proximity to the implanted device, a more accurate determination as to the presence of an infection may be made. In addition, in some embodiments, the frequency with which a second patient parameter is monitored is kept low until a first indicator of infection crosses a threshold, allowing power to be saved by not frequently monitoring the second patient parameter at a time where infection is not likely. Power conservation may be particularly beneficial to implanted medical devices having a battery component. These and other advantages will be readily understood from the following detailed descriptions when read in conjunction with the accompanying drawings.

Figure 1:
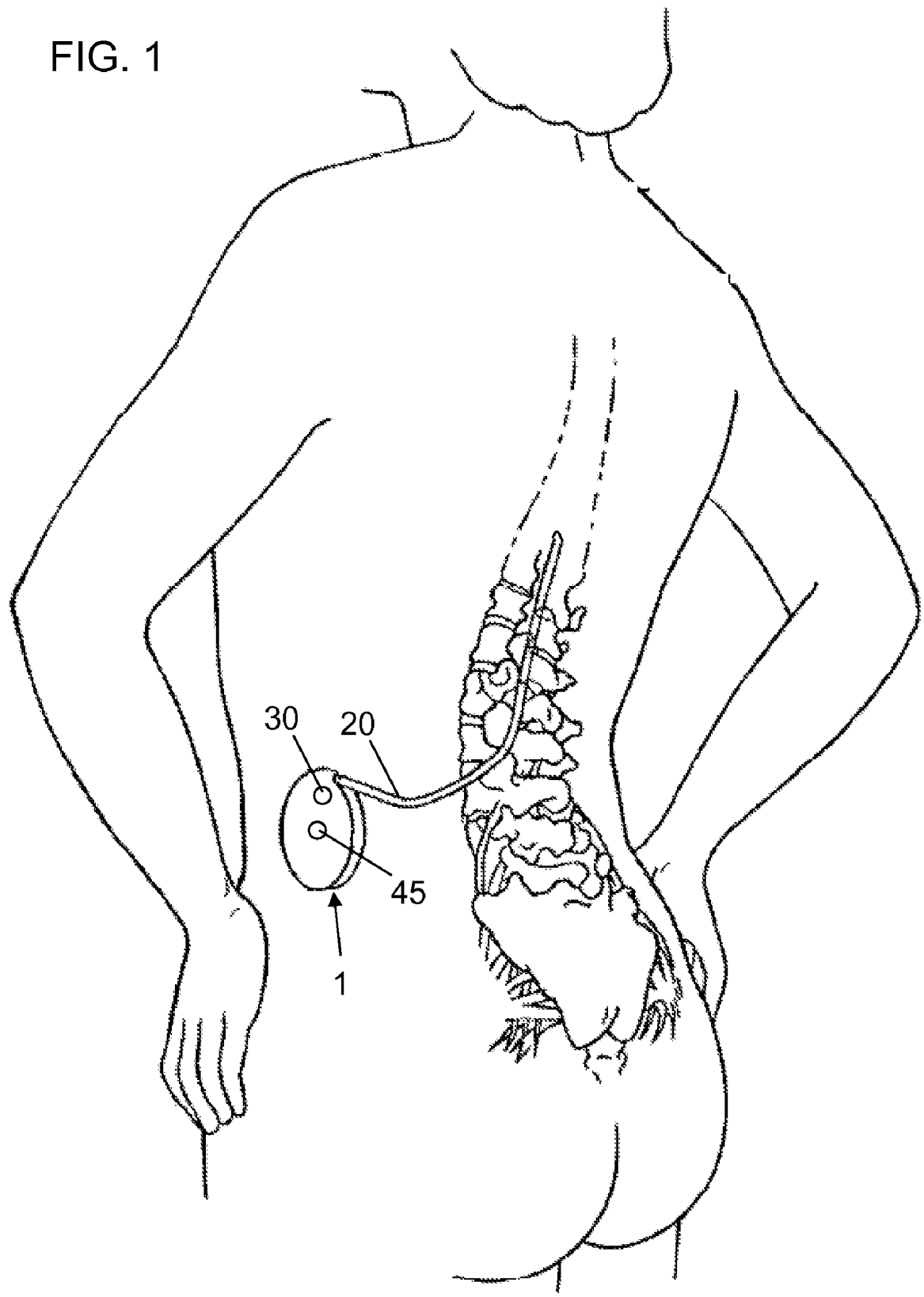
FIG. 1 is a diagrammatic representation of a perspective view of an environment of an implantable infusion system implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "active implantable medical device" means an implantable medical device that includes a power source to deliver therapy to a patient. Non-limiting examples of active implantable medical devices include implantable infusion devices and implantable electrical signal generators, such as cardiac defibrillators, pacemakers, neurostimulators, gastric stimulators, and cochlear implants. Active implantable medical devices typically are used in conjunction with associated implantable medical devices, such as catheters or leads.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices and methods that may be used to monitor infection in proximity to an implanted medical device. The systems, devices and methods monitor two or more patient parameters, at least one of which is an indicator of infection. In some embodiments, a second patient parameter is also an indicator of infection that may be used as verification that the first indicator is indicative of an infection. In some embodiments, the second patient parameter is a physiological parameter that provides information regarding whether the first indicator is indicative of infection. For example, increased temperature in proximity to an implanted device may be indicative of infection, but may also be indicative of increased patient activity. Accordingly, monitoring of patient activity in combination with temperature in proximity to the implanted device may serve to increase the accuracy of determinations as to whether increased temperature is indicative of infection.

The teachings described herein may be employed in conjunction with nearly any implantable medical device, including monitoring devices. In some embodiments described herein, benefit may be seen with active implantable medical devices—i.e., those having a power source for providing therapy, which power source may otherwise be drained by the constant monitoring of infection during time periods where infection is not likely to be observed. For example, in some embodiments, the frequency of monitoring of a second patient parameter is kept low until a first indicator of infection crosses a threshold, allowing power to be saved by not frequently monitoring the second patient parameter at a time where infection is not likely.

Figure 2:
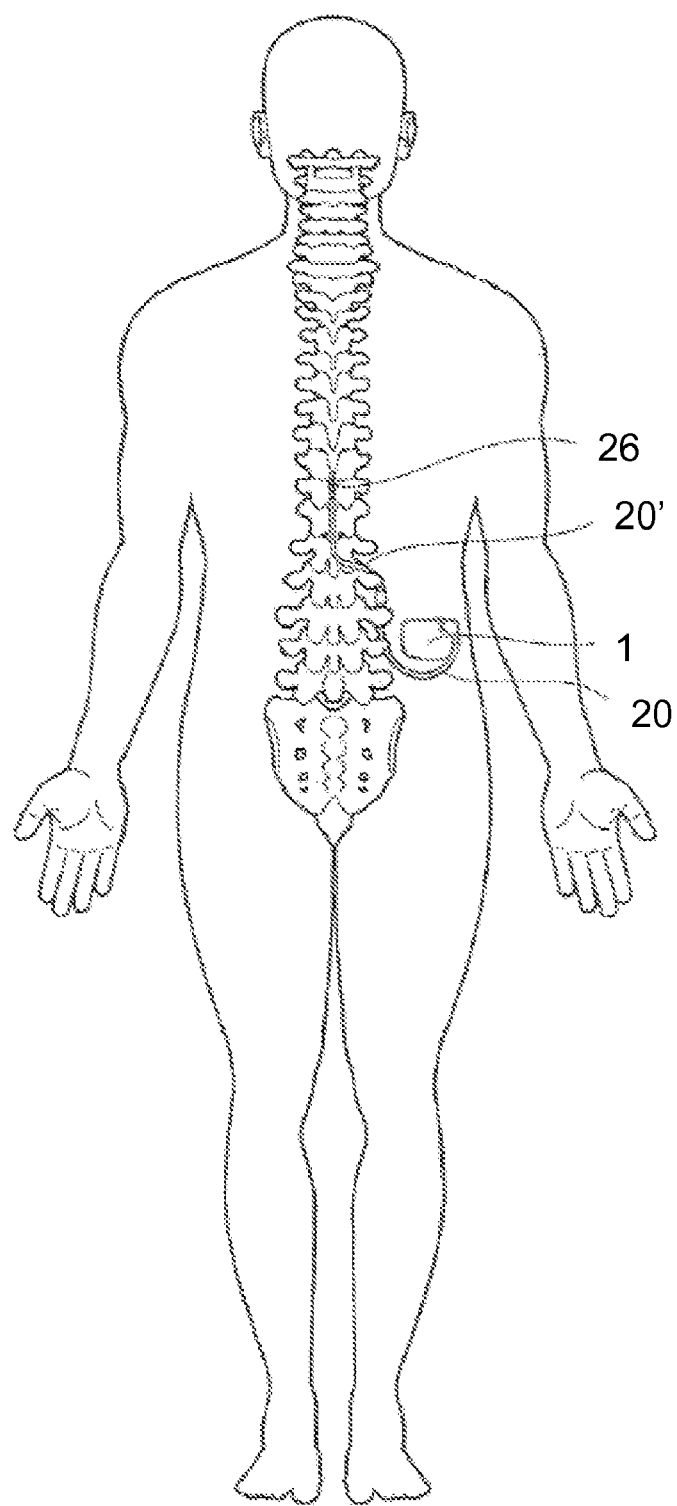
FIG. 2 is a diagrammatic representation of a perspective view of an environment of an implantable electrical signal generator system implanted in a patient.
Figure 3A:
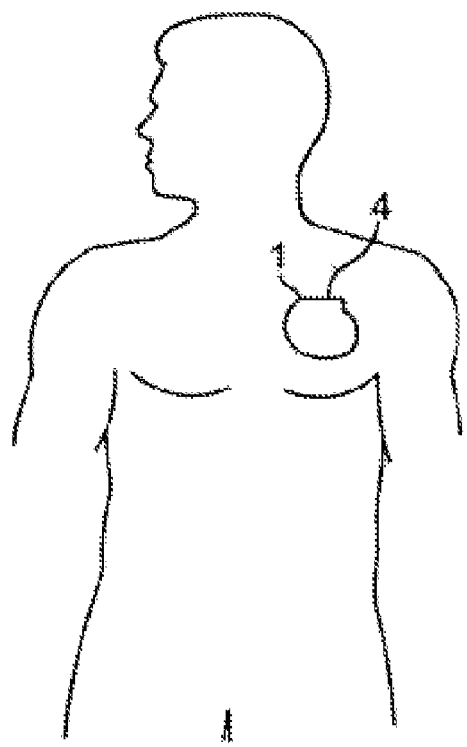
FIGS. 3A-D are a diagrammatic representations of a perspective views of environments of implantable medical devices implanted in patients.
Figure 3B:
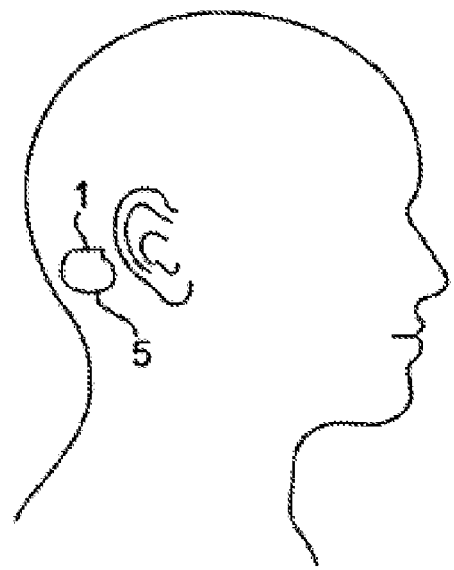
Figure 3C:
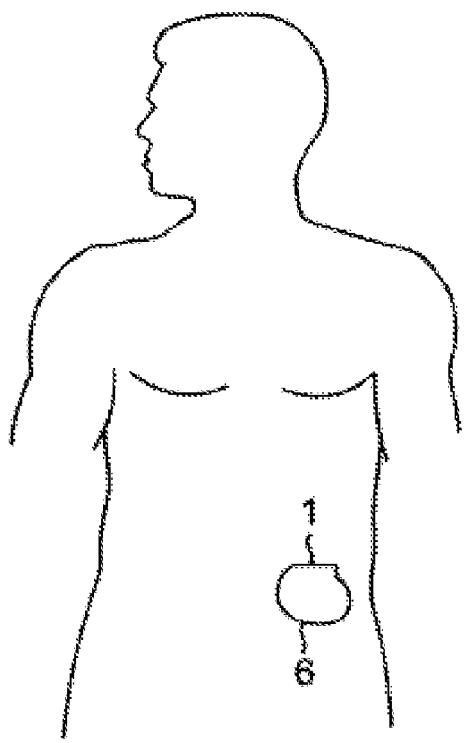
Figure 3D:
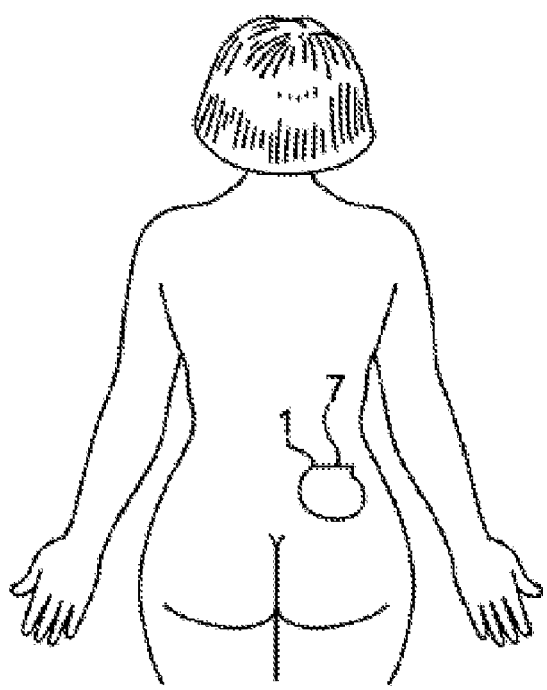

Referring to FIGS. 1 and 2, general representative environments for implanting active medical devices 1 and associated devices 20 are shown. Active medical device 1 is subcutaneously implanted in an abdominal region of a patient. A distal portion of associated device 20 is intrathecally inserted into the patient's spinal canal through a lumbar puncture and advanced rostrally to a desired location (FIG. 1) or epidurally placed along a suitable location of spinal cord (FIG. 2). Proximal end of associated device 20 is tunneled subcutaneously to location of active device 1, where it may be connected to active device 1. While distal portion of associated device 20 is shown in FIGS. 1 and 2 as being located in or on spinal cord, it will be understood that associated device 20 may be placed at any location in patient for which it is desirable to administer therapy generated or delivered by active medical device 1.

In the embodiment shown in FIG. 1, active implantable device 1 is an infusion device, and associated device 20 is a catheter. Catheter 20 is typically a flexible tube with a lumen running from the proximal end of catheter 20 to one or more delivery regions that are typically located at the distal portion of catheter 20. Proximal portion of catheter 20 is connected to infusion device 20. Distal portion of catheter 20 is positioned at a target location in the patient to deliver fluid containing therapeutic agent from infusion device 1 to patient through a delivery region of catheter 20. Infusion device 1, such as Medtronic Inc.'s SynchroMed™ II implantable programmable pump system, includes a reservoir (not shown) for housing a therapeutic substance and a refill port 45 in fluid communication with reservoir. The reservoir may be refilled by percutaneously inserting a needle (not shown) into patient such that needle enters refill port 45, and fluid containing therapeutic substance may be delivered into reservoir from needle via refill port 45. Infusion device 1 shown in FIG. 1 also includes a catheter access port 30 that is in fluid communication with the catheter 20. Fluid may be injected into or withdrawn from patient through catheter 20 via catheter access port 30 by percutaneously inserting a needle into access port 30. Each entry of needle across patient's skin to gain access refill port 45 or access port 30 results in the possibility of infection in proximity to the active medical device 1.

In the embodiment shown in FIG. 2, active implantable device 1 is an electrical signal generator, such as Medtronic Inc.'s Restore™ Advanced implantable neurostimulator, and associated devices 20, 20' are a lead extension 20 and lead 20'. Lead 20' includes one or more electrical contacts (not shown) on its proximal end portion and one or more electrodes on its distal end portion 26. The contacts and electrodes are electrically coupled via wires running through lead 20'. Electrical signals generated by the signal generator 1 may be delivered to lead 20 through the contacts and then to the patient through the electrodes. As shown in FIG. 2, lead 20' may be connected to signal generator 1 through a lead extension 20. Extension 20 includes one or more contacts at the proximal and distal end portions that are electrically coupled through wires running through extension 20. Of course it will be understood that with some systems lead 20' may be directly connected to electrical signal generator 1 without use of a lead extension 20. It will be further understood that more than one lead 20' or lead extension 20 may be employed per signal generator 1.

While FIGS. 1 and 2 depict systems including as active implantable medical devices 1 infusion devices and electrical signal generators, it will be understood that the teachings described herein may be applicable to virtually any known or future developed active implantable medical device and that virtually any non-active implantable medical device may be appropriately adapted and configured to perform according to the teachings provided herein.

Referring to FIG. 3, alternative locations for implanting a medical device 1 are shown. As depicted in FIG. 3A, device 1 may be implanted in the pectoral region 7 of a patient. Alternatively, device 1 may be implanted in the head of a patient, more specifically behind the patient's ear (FIG. 3B), in the patient's abdomen (FIG. 3C) or in the patient's lower back or buttocks (FIG. 3D). Of course, device 1 may be placed in any medically acceptable location in patient.

Figure 4:
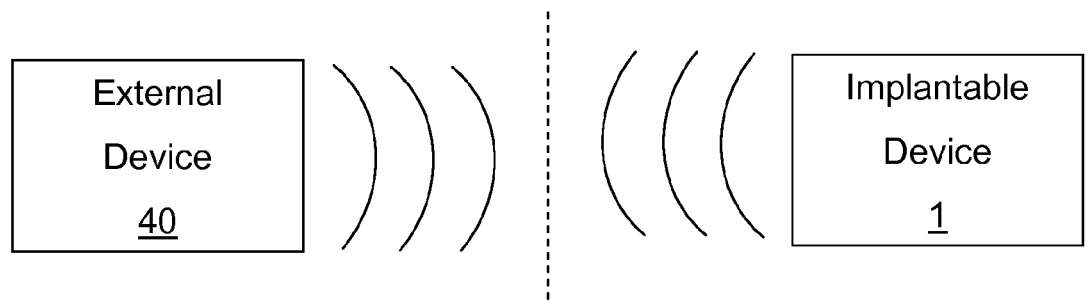
FIG. 4 is a diagrammatic representation of an external device and a implantable medical device in wireless communication.

Referring to FIG. 4, an external device 40 in wireless communication with implantable device 1 is shown. External device 40 may communicate with implantable device 1 through patient's skin, which is represented by the dashed line in FIG. 4. In various embodiments, implantable device 1 carries out the various infection monitoring methods, or portions thereof, described herein. In some embodiments, the combination of implantable device 1 and external device 40 carry out the various infection monitoring methods, or portions thereof, described herein. In various embodiments, where implantable device 1 is a programmable device, external device 40 may be a programmer device, such as Medtronic Inc.'s N'Vision™ clinician programmer. Of course external device may be any device capable of wirelessly communicating with implantable device 1, such as a patient programmer, a computer, a personal data assistant, or the like. External device 40 and implantable device 1 may be capable of one-way (external device 40 to implantable device 1 or implantable device 1 to external device 40) or two-way communication.

Figure 5A:
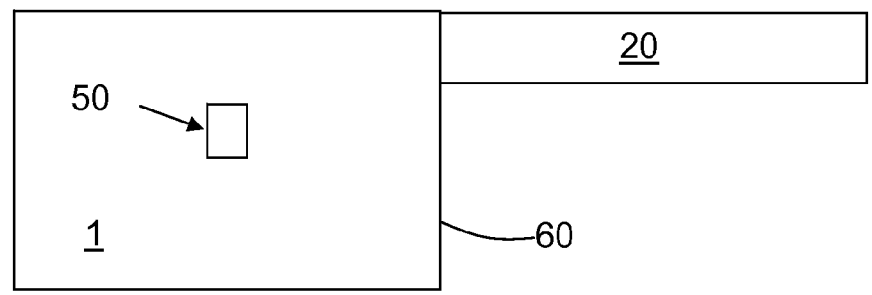
FIGS. 5A-B is a diagrammatic representation of a side view (5A) and back view (B) of an implantable medical device system having sensor(s) in proximity to the implantable device.
Figure 5B:
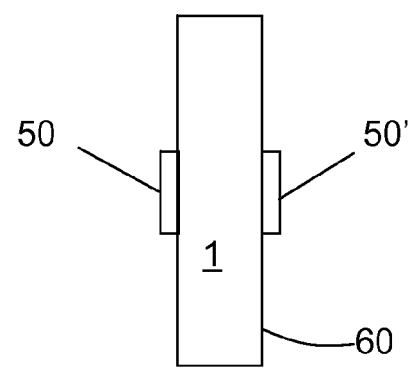

Referring to FIG. 5, sensor(s) 50, 50' associated with implantable active medical device 1 is shown. FIG. 5A is a side view of a representative active device 1 and associated device 20. FIG. 5B is a back view of a representative active device 1. One or more sensor 50, 50' may be located in proximity to device 1; e.g., disposed on, in, or near housing 60 of device 1. Sensor 50, 50' may be any device capable of detecting and transmitting information regarding an indicator of infection to device 1 or capable of detecting and transmitting information that may be useful in determining whether an indicator of infection may actually be indicative of infection. If housing 60 is hermetically sealed, feedthroughs (not shown) may be used to provide electrical connectivity through housing 60 while maintaining the hermetic seal. While not shown, it will be understood that one or more sensor capable of detecting an indicator of infection may be located on, in, or about accessory device 20. Examples of physical or chemical stimuli that may serve as indicators of infection are temperature, impedance, pH, and biological markers of infection. Examples of parameters that may provide information useful for determining whether an indicator of infection may actually be indicative of infection include parameters indicative of patient activity.

Changes in temperature in proximity to implanted device 1 may be used as an indicator of infection in proximity to device 1. The temperature of body tissue at a site of infection is generally greater than that of body tissue at a location removed from the site of infection. Accordingly, an increase in temperature in proximity to an implanted medical device 1 may serve as an indicator of infection. Any suitable sensor 50, 50' capable of detecting temperature or changes in temperature may be employed. For example, temperature sensor 50, 50' may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, or the like.

Changes in impedance of tissue in proximity to implanted device 1 may be used as an indicator of infection in proximity to device 1. For example, an increase in fluid in tissue is often observed at a site of an infection. Accordingly, a decrease in impedance of tissue in proximity may serve as an indicator of infection. In the case of impedance measurement, detection or monitoring, sensors 50, 50' are electrodes. Impedance may be measured between two electrodes. Current or voltage is applied between the electrodes with one electrode at any given time serving as a source and the other serving as a sink. In various embodiments, electrodes will be positioned at opposing surfaces of housing 60 of device 1. In other embodiments, one electrode may be located on accessory device 20, e.g. on a lead, and one may be located on housing of device 1. Alternatively, one electrode may be located on accessory device 20 and housing 60 of device 1 may serve as a return electrode, in a manner similar to unipolar signal generators. Further, it will be understood that more than one electrode pair may be employed to monitor impedance.

In instances where device 1 is an electrical signal generator, the electrical components used for generating therapeutic electrical signals may also be used for generating signals for impedance monitoring. In instances where device 1 is not an electrical signal generator, e.g. device 1 is an infusion pump, components capable of generating appropriate electrical signals for testing impedance of body tissue may be incorporated into device 1. Any impedance detection components or circuitry may be employed. For example, an ohm meter or a wheatstone bridge design may be used to measure or detect changes in impedance or resistance. Examples of suitable components or circuitry are described in, for example, the following patents and applications assigned to Medtronic, Inc.: U.S. 2006/0259079; U.S. 2006/0036186; U.S. 2004/0162591; U.S. 2003/0176807; U.S. Pat. No. 5,876,353; U.S. Pat. No. 5,824,029; and U.S. Pat. No. 5,282,840.

Changes in pH in proximity to implanted device 1 may be used as an indicator of infection in proximity to device 1. As pH may serve as a general indicator of the state of a tissue, a change in pH may be indicative of infection. Accordingly, a sudden or gradual change in pH in proximity to an implanted medical device 1 may serve as an indicator of infection. Any suitable sensor 50, 50' capable of detecting pH or changes in pH may be employed.

Any biological marker of infection may be detected in accordance with the teachings presented herein. Non-limiting examples of biological markers of infection include viral, fungal, or bacterial proteins or nucleic acids or fragments thereof. As most infections associated with implantable medical devices appear to be due to infection due to *Staphlococcus aureus, Staphlococcus epidermis, Pseudomonus auruginosa* and *Candidia*Sp., detection of proteins, nucleic acids, or fragments thereof of such microorganisms may be beneficial. Alternatively, detection of indicators of an immune response may be detected. For example, an increase in a pro-inflammatory cytokine. Non-limiting examples of proinflammatory cytokines include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors. Indication of an immune response may also be detected by an decrease in an anti-inflammatory cytokine in proximity to device 1. Non-limiting examples of anti-inflammatory cytokines include IL-4, IL-10, IL-17, IL-13, IL-1α, and TNFα receptor. It will be recognized that some of proinflammatory cytokines may act as anti-inflammatory cytokines in certain circumstances, and vice-versa. Such cytokines are typically referred to as plieotropic cytokines. An immune response may also be detected by measuring changes (baseline versus after device implant or other event, a first point after device implant or other event versus a second point after device implant or other event, etc.) in the presence of other factors involved in an immune response. Non-limiting examples of such other factors include TGF, PDGF, VEGF, EGF, FGF, I-CAM, and nitric oxide. In addition, an immune response may be detected by changes in chemokines, such as 6cKine and MIP3beta, and chemokine receptors, including CCR7 receptor. Further, an immune response may be measured by changes in immune cell population (upregulated Langerhans cells, dendritic cells, lymphocytes), or immune cell surface co-stimulatory molecules (Major Histocompatibility, CD80, CD86, CD28, CD40). An immune response may also be detected by measuring changes in other factors involved in the inflammatory cascade, for example in the signal transduction cascades including factors such as NFκ-B, Egr-1, Smads, toll-like receptors, and MAP kinases. In addition, an immune response may be detected by a change in the presence of an exogenous antigen believed to have caused an inflammatory response, such as, e.g., a bacteria, a virus, or a fungus.

Any sensor capable of detecting such biological markers indicative of infection may be used. In various embodiments, a biosensor is used to detect the presence of a molecule in proximity to implanted device 1. Any known or future developed biosensor may be used. The biosensor may have, e.g., an enzyme, an antibody, a receptor, or the like operably coupled to, e.g.,a suitable physical transducer capable of converting the biological signal into an electrical signal. In some situations, receptors or enzymes that reversibly bind the molecule being detected may be preferred. In various embodiments, sensor 50, 50' includes an electrode with an ion selective coating that is capable of directly transducing the amount of a particular substance. An example of this type of transducer is described in the paper "Multichannel semiconductor-based electrodes for in vivo electrochemical and electrophysiological studies in rat CNS" by Craig G. van Home, Spencer Bement, Barry J. Hoffer, and Greg A. Gerhardt, published in Neuroscience Letters, 120 (1990) 249-252. In various embodiments, sensor 50, 50' may be a sensor as described in, e.g., U.S. Pat. No. 5,978,702, entitled TECHNIQUES OF TREATING EPILEPSY BY BRAIN STIMULATION AND DRUG INFUSION or U.S. 2005/0209513, entitled COLLECTING SLEEP QUALITY INFORMATION VIA A MEDICAL DEVICE, filed Apr. 15, 2004, and published Sep. 22, 2005. Modifications of the teachings presented in the above-cited references may be made to account for one or more biological marker of infection.

For the above-discussed indicators of infection or other indicator of infection, it may be desirable to compare levels of the indicators at a location in proximity to device 1 and at a location removed from device. Such comparisons may allow for a reduction in false positive detections. For example, elevation in temperature in proximity to device 1 may be due to localized infection or may be due to increased activity of the patient; increases in inflammatory cytokines in proximity to the device may be due to localized infection or a more general immune response; etc. By comparing the level of an indicator of infection in proximity to an implanted device to the level at a location removed from the device, a more accurate determination of whether an infection is present in proximity to the device may be made. Additional information regarding monitoring an indicator of infection at two locations is provided in US Patent Application Ser. No. 11/737, 171, titled "Implantable Therapy Delivery System Having Multiple Temperature Sensors,"filed on even date herewith, naming Martin Gerber and John Rondoni as inventors, which application is hereby incorporated herein by reference in its entirety to the extent it does not conflict with the disclosure presented herein.

Sensors 50 capable of detecting other patient parameters may also be employed. Information regarding parameters other than indicators of infections may be used to determine whether the probability of information regarding an indicator of infection being indicative of an infection is more or less likely in light of the information regarding the other parameter. The other parameter may be valuable for such a determination with a given indicator or set of indicators of infection, but may not be valuable for other indicators or sets of indicators of infection. In general, patient parameters relating to activity may be useful. For example, information regarding patient activity may be useful for determining whether information regarding temperature may be more or less indicative of infection; e.g., if activity increases, an increase in temperature may be less likely to indicate infection. That is, such a temperature increase in proximity to implanted device 1 is more likely to be due to increased patient activity and thus increased overall body temperature of patient, rather than due to a localized temperature increase due to infection.

Any suitable sensor may be used to measure a parameter related to patient activity, such as patient movement or a physiological parameter associated with patient activity. For example, activity sensors, capable of detecting patient movement, such as an accelerometer, a bonded piezoelectric crystal, a mercury switch, or a gyro may be used to detect, e.g., body motion, footfalls or other impact events, or the like. Processor 110 may determine an activity level based on a signal generated by one or more of these types of sensors 50 by sampling the signal and determining a number of activity counts during the sample period. Processor 110 may then store the determined number of activity counts in memory 120 as an activity level. Further information regarding activity sensing and associated processing of data related to activity sensing may be found in U.S. Pat. No. 7,167,743, entitled "Collecting Activity Information to Evaluate Therapy" and issued Jan. 23, 2007.

In various embodiments, a physiological parameter that may serve as an indicator of patient activity may be monitored. For example, sensor 50 may detect a signal that indicates the heart rate, ECG morphology, respiration rate, respiratory volume, core temperature, subcutaneous temperature, or muscular activity of the patient. In such embodiments, processor 110 may periodically determine the heart rate, measured value of one or more ECG morphological features, respiration rate, respiratory volume, core temperature, subcutaneous temperature, or muscular activity level of patient based on the signal. The determined values of these parameters may be mean or median values.

Sensors 40 may include electrodes located on associated device 20 or integrated as part of the housing of implantable active device 1 that generates an electrogram signal as a function of electrical activity of the heart of patient, and processor 110 may periodically determine the heart rate of patient based on the electrogram signal. In other embodiments, a sensor 50 may include an acoustic sensor within device 1. The signals generated by such sensors 50 may vary as a function of contraction of the heart of patient, and can be used by processor 110 to periodically determine the heart rate of patient.

In some embodiments, processor 110 may detect, and measure values for one or more ECG morphological features within an electrogram generated by electrodes as described above. ECG morphological features may vary in a manner that indicates the activity level of the patient. For example, the amplitude of the ST segment of the ECG may increase with increased patient activity. Further, the amplitude of the QRS complex or T-wave may increase, and the widths of the QRS complex and T-wave may decrease with increased patient activity. The QT interval and the latency of an evoked response may decrease with increased patient activity, and the amplitude of the evoked response may increase with increased patient activity.

In some embodiments, sensors 50 may include an electrode pair, e.g. including one electrode integrated with the housing of device 1 and one integrated with associated device 20, that generates a signal as a function of the thoracic impedance of patient, which varies as a function of respiration by patient. The electrodes of the pair may be located on opposite sides of the patient's thorax. For example, the electrode pair may be integrated with associated device 20 and may be located proximate to the spine of a patient for delivery of therapy, and device 1 with an electrode integrated in its housing may be implanted in the abdomen of patient. Processor 110 may monitor the signals generated by such sensors 50 to periodically determine a respiration rate and/or respiratory volume of patient. An electrogram generated by electrodes as discussed above may also be modulated by patient respiration, and processor 110 may use the electrogram as an indirect representation of respiration rate.

In some embodiments, sensors 50 may include one or more electrodes that generate an electromyogram (EMG) signal as a function of muscle electrical activity. The amplitude and/or frequency of an EMG signal may vary based on the activity level of a patient. The electrodes may be, for example, located in the legs, abdomen, chest, back or buttocks of patient to detect muscle activity associated with walking, running, or the like.

Figure 6:
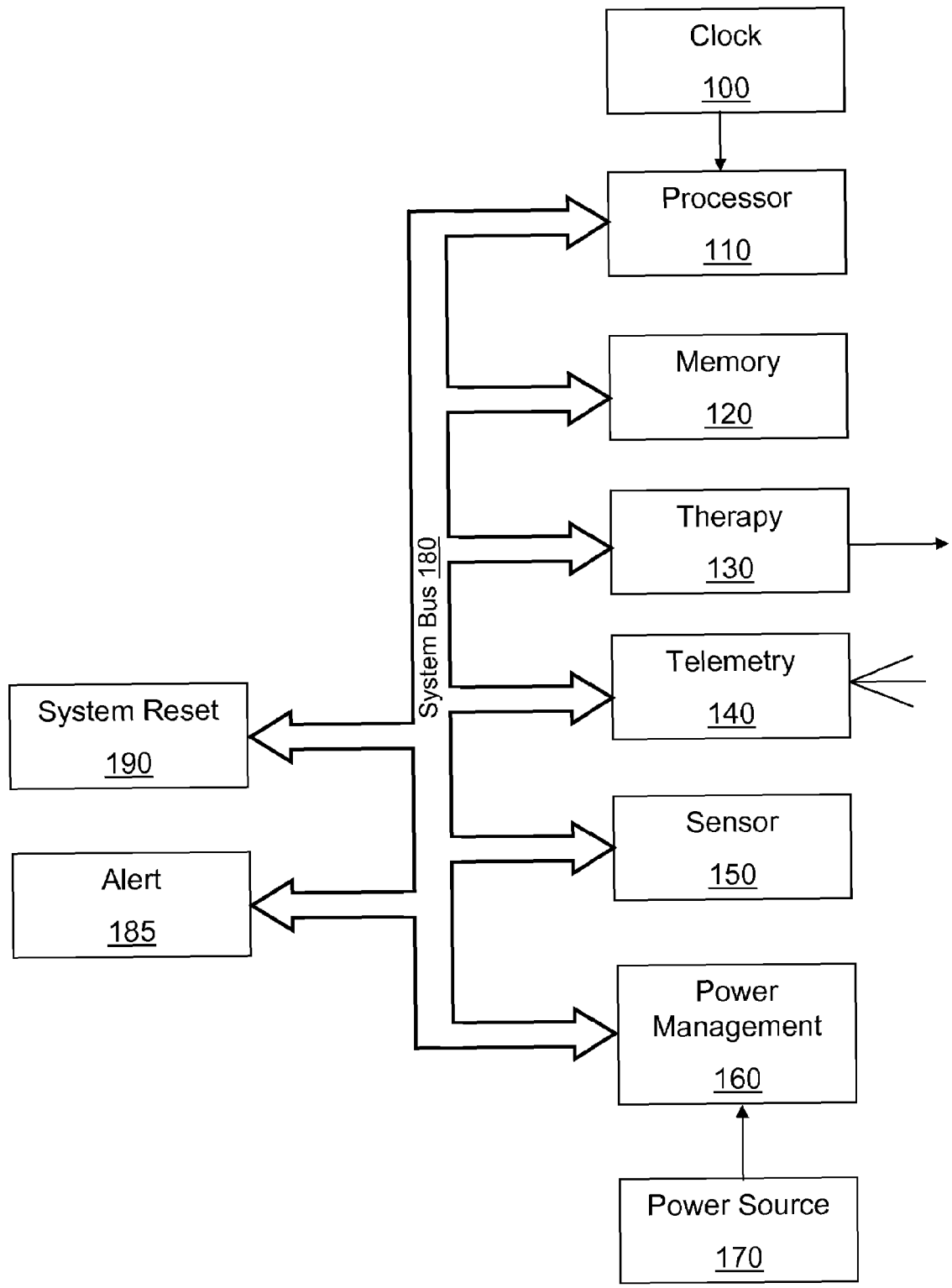
FIG. 6 is a schematic block diagram of representative components of a representative implantable medical device.

Referring to FIG. 6, some representative electronic components of an implantable medical device 1 according to various embodiments are shown in block form. Active implantable medical device 1 as depicted in the embodiment shown in FIG. 6 includes a clock 100, a processor 110, a memory 120, a therapy output or delivery component 130, a telemetry component 140, a sensor 150, a power management module 160, a power source 170, an alert module 185, and a system reset module 190. Other components of active implantable medical device 1 can include, e.g., a diagnostics module (not shown). All components except the power source 170 can be configured on one or more Application Specific Integrated Circuits (ASICS) or may be one or more discrete components, or a combination of both. Also, all components, except the clock and power source are connected to bi-directional data bus 180 that is non-multiplexed with separate address and data lines.

Processor 110 may be synchronous and typically operates on low power, such as Motorola 68HC11 synthesized core operating with a compatible instruction set. Clock 100 counts the number of seconds since a fixed date for date/time stamping of events and may be used for therapy control. Memory 120 includes memory sufficient for operation of device 1, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as telemetry module 140 or sensor module 150, so that the selected modules can request control of data bus 180 and write data directly to memory 120 bypassing processor 110. System Reset 190 controls operation of ASICs and modules during power-up of device 1, so ASICs and modules registers can be loaded and brought on-line in a stable condition.

Telemetry 140 module or other wireless module provides for communication between implantable device 1 and external device 40 such as a programmer. Communication may be bi-directional. Telemetry module 140 generally includes a telemetry antenna, a receiver, a transmitter, and a telemetry processor. Telemetry modules are generally known in the art and are further detailed in U.S. Pat. No. 5,752,977, entitled "Efficient High Data Rate Telemetry Format For Implanted Medical Device" issued to Grevious et al. (May 19, 1998). While module 140 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Therapy module 130 refers to components for carrying out the delivery or generation of therapeutic output to be delivered to a patient from active device 1. One of skill in the art will appreciate that the components may vary on a device-by-device basis and a therapy-by-therapy basis. For example, therapy module 130 may contain an oscillator if device 1 is an electrical signal generator and may contain a pumping mechanism if device 1 is an infusion device.

Sensor module 150 includes a sensor 50, 50', e.g. as discussed with regard to FIG. 5, and may include other components for transmitting sensed information from sensor 50, 50' to, e.g., processor 110 or memory 120. Sensor module 150 or other components of device 1 may include one or more analog to digital converters to convert analog signals generated by sensor 50 into digital signals usable by processor 110, as well as suitable filter and amplifier circuitry.

Alert module 185 may issue an alert, e.g. an audible alert or tactile alert, such as a vibration. An alert may be issued if information indicative of an infection is detected. The alert will serve to prompt the patient to seek medical attention.

It will be understood that the components described in FIGS. 1-6 are but examples of components that an implantable device 1 may have and that many other device or system configurations may be employed to carry out the methods described below. However, for the sake of convenience, the discussion that follows with regard to the methods illustrated in the flow diagrams of FIGS. 7 and 9-11 and the block diagram of FIG. 8 will refer to components as described with regard to FIGS. 1-6.

Figure 7:
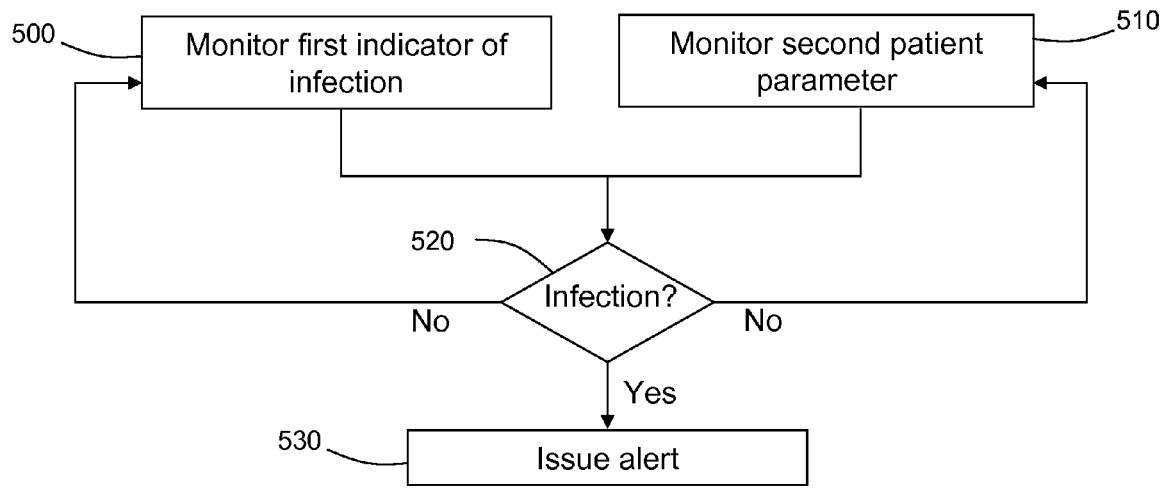
FIG. 7 is a flow diagram of a representative method.

Referring to FIG. 7, a flow diagram of a representative method is shown. According to various embodiments, a method for monitoring an infection in proximity to a medical device includes monitoring a first indicator of infection in proximity to a medical device implanted in a patient (500) and monitoring a second patient parameter (510). Monitoring may include transmitting information from one or more sensor 50 to processor 110 or memory 120. The method further includes determining whether the combination of the first indicator and the second parameter are indicative of infection in proximity to the implanted device (520). Examples of how such a determination may be made are discussed below with regard to FIGS. 8-11. If the combination of the first indicator and the second parameter are indicative of an infection, an alert may be issued (530). The alert may include a sensory indication, such as an audible indication or a tactile indication, such as a vibration, or visual indication. A visual indication may include, for example, text or an image. The alert may be issued by implanted device 1 or an external device 40 (see, e.g., FIG. 4), such as a programmer. If the indication is visual, the alert will be presented to the patient or clinician by an external device. If the combination of the first indicator and the second parameter are not indicative of an infection, the process of monitoring the first indicator (500), monitoring the second indicator (510), and determining whether the combination of the first indicator and the second parameter are indicative of infection in proximity to the implanted device (520) may continue. Of course, the process may continue after the alert is issued (530). Alternatively, the process or steps thereof may be stopped to conserve power.

Figure 8:
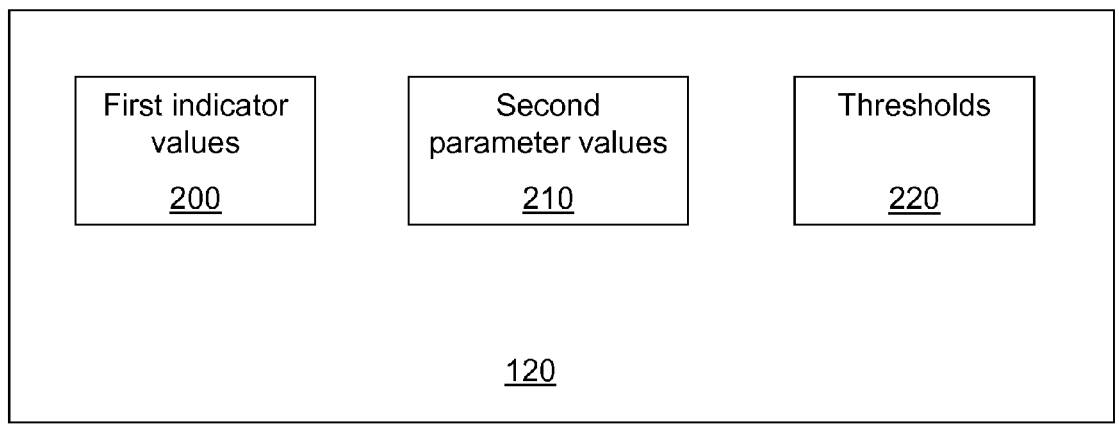
FIG. 8 is block diagram of portions of a representative memory.

By way of example, and referring to FIGS. 8-10, a determination of whether information related to the first indicator and the second parameter are indicative of an infection in proximity to the implanted medical device (520) may be made in many ways. Referring to FIG. 8, memory 120, according to various embodiments, is shown in more detail. Memory 120 stores information related to first indicator of infection values 200, second patient parameter values 210, and threshold values 220. Threshold values 220 may be values specified by an external device 40, such as a physician programmer, and may be specifically tailored to a particular patient. Threshold values 220 may be based on the first indicator of infection being monitored, the second patient parameter being monitored, or a combination of both the first indicator and the second parameter. Information stored in memory 120 relating to indicator values 200 or parameter values 210 may be values obtained at a particular point in time, mean or median values, values over time, or the like. Similarly, threshold values 220 may be related to individual values, mean or median values, values over time, or the like. In some embodiments, processor 110 compares a determined first indicator value 200 and a second parameter value 210 to a look-up table of threshold values 220 stored in memory 120 to determine whether the combination of the first indicator and the second parameter are indicative of infection (520).

In some embodiments, processor 110 may compare values 200, 210 calculate threshold values 220 based on information monitored within the patient by device 1. For example, a threshold value 220 may be deviation of 50% or greater, 40% or greater, 30% or greater, 20% or greater, 10% or greater, 5% or greater, etc. from a mean or median value 200, 210 monitored within the patient over a period of time. Processor 110 may compare a value 200, 210 to a calculated threshold value 220. Of course, in such instances, possessor 110 may compare a value 200, 210 to a mean or median value 200, 210 determined over time to determine whether a threshold has been crossed without first storing such threshold value 220 in memory 120.

Figure 9A:
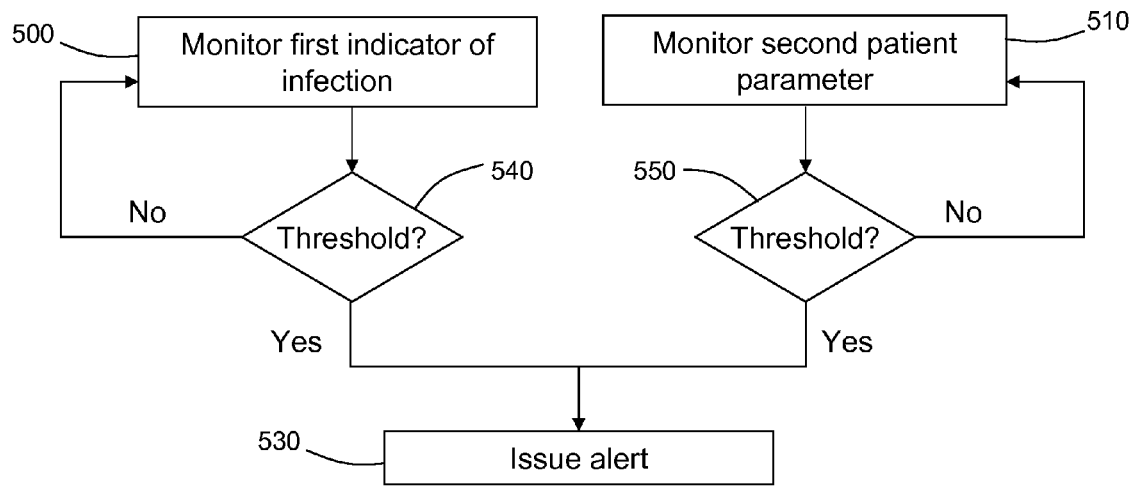
FIGS. 9-11 are flow diagrams of representative methods.
Figure 9B:
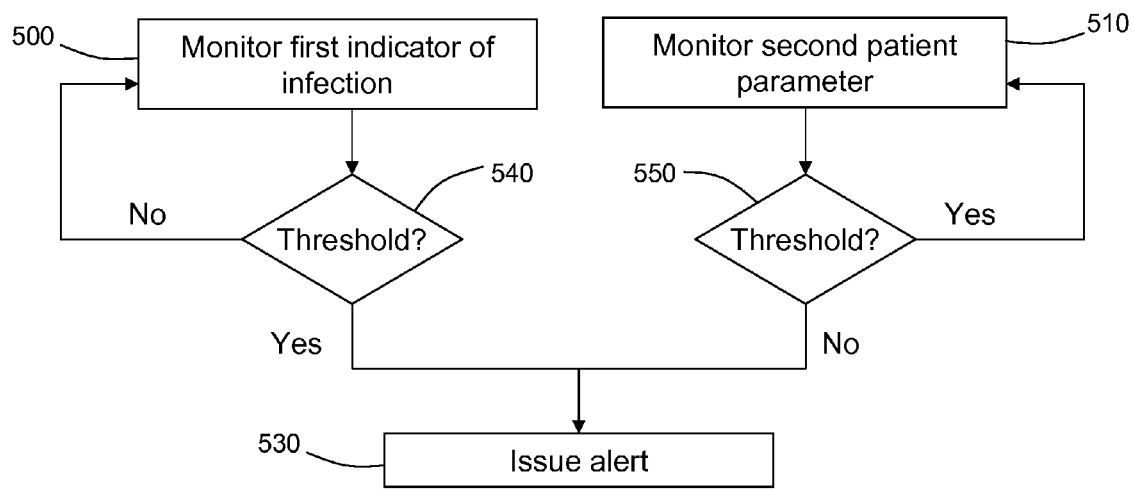

Referring to FIG. 9, processor 110 may compare first indicator of infection values 200 to threshold values 220 to determine whether the first indicator has crossed a threshold (540) and may compare second patient parameter values (210) to threshold values (220) to determine whether the second parameter has crossed a threshold (550). As shown in FIG. 9A, if the first indicator and second indicator have crossed thresholds, an alert is issued (530). Such a configuration is desirable when deviation of a second patient parameter is indicative of an infection; e.g., when the second patient parameter is a second indicator of infection in proximity to the device. Thus, the second indicator can serve to verify that the first indicator is likely to be indicative of an infection. As shown in FIG. 9B, if the first indicator has crossed a threshold and second indicator has not crossed a threshold, an alert is issued (530). Such a configuration is desirable when deviation of a second patient parameter discounts the likelihood of infection associated with the first indicator; e.g., when the first indicator of infection is temperature and the second patient parameter is indicative of patient activity. Thus, the second indicator can serve to prevent a false positive determination based on information regarding the first indicator.

Figure 10A:
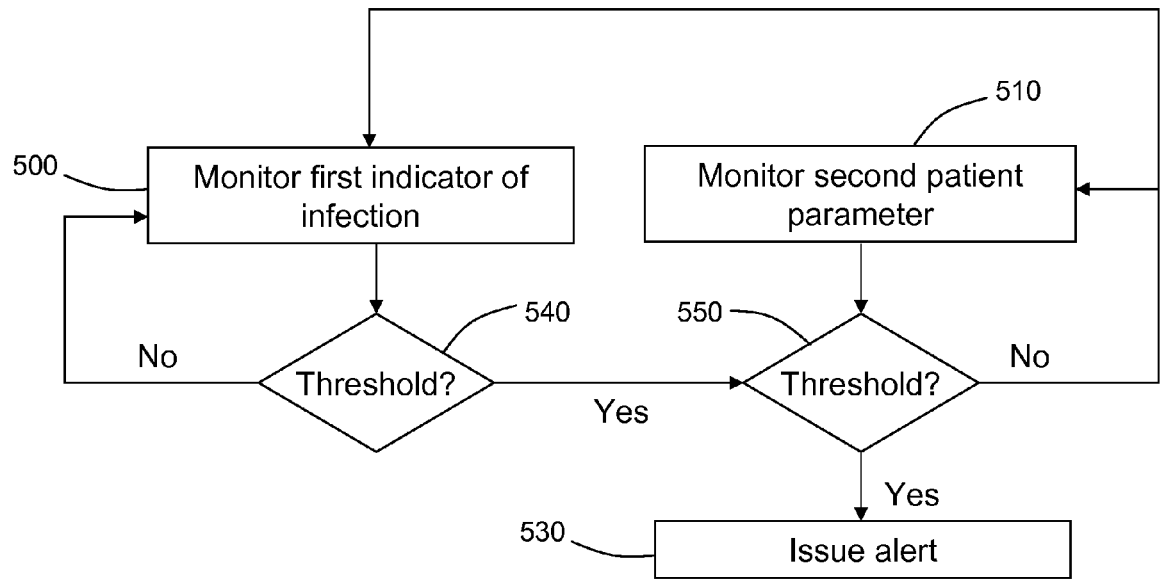
Figure 10B:
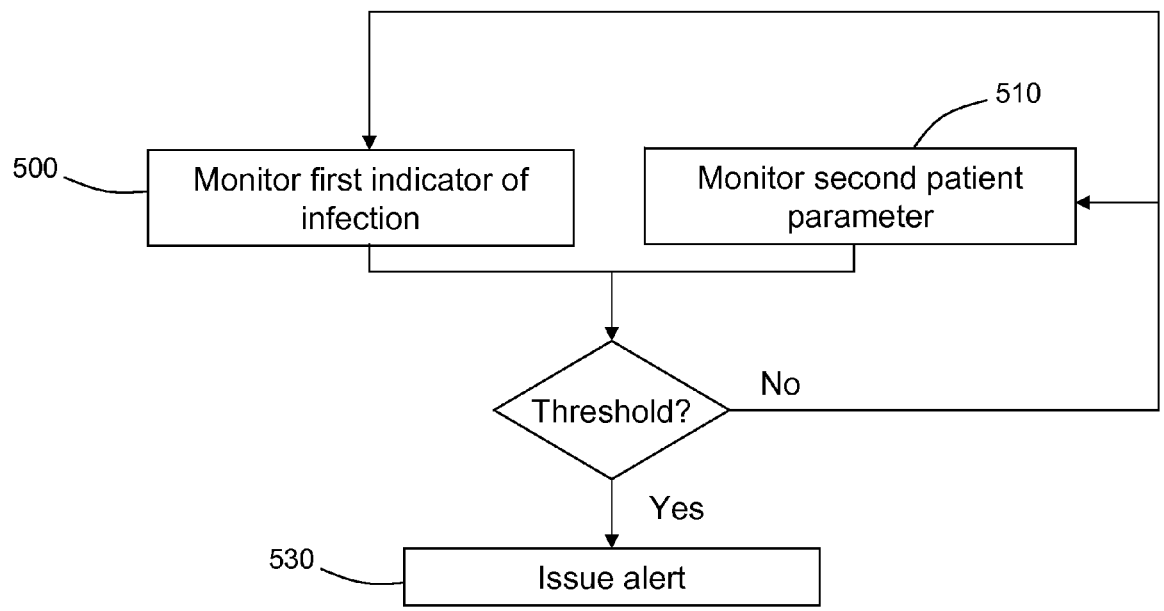

FIGS. 10A-10B show alternative methods of monitoring infection. As shown in FIG. 10A, a determination may be made as to whether a value associated with the monitored first indicator has crossed a threshold (540), and thus indicating the possibility of an infection being present in proximity to implanted device 1, prior to determining whether a value associated with the monitored second parameter has crossed a threshold (550). If the value associated with the second parameter has crossed a threshold (or has not—e.g., as in FIG. 9B), an alert may be issued (530). If the value associated with the second parameter has not (or has) crossed a threshold, the process of monitoring the first indicator (500), monitoring the second parameter (510), determining whether a value associated with the first indicator has crossed a threshold (540), and determining whether a value associated with the second parameter has crossed a threshold (540) may be continued.

As shown in FIG. 10B, combined information regarding values associated with the monitored first indicator and the monitored second parameter may be used to determine whether a threshold has been crossed (540). If the threshold has been crossed based on the combined data, an alert may be issued (530).

Figure 11:
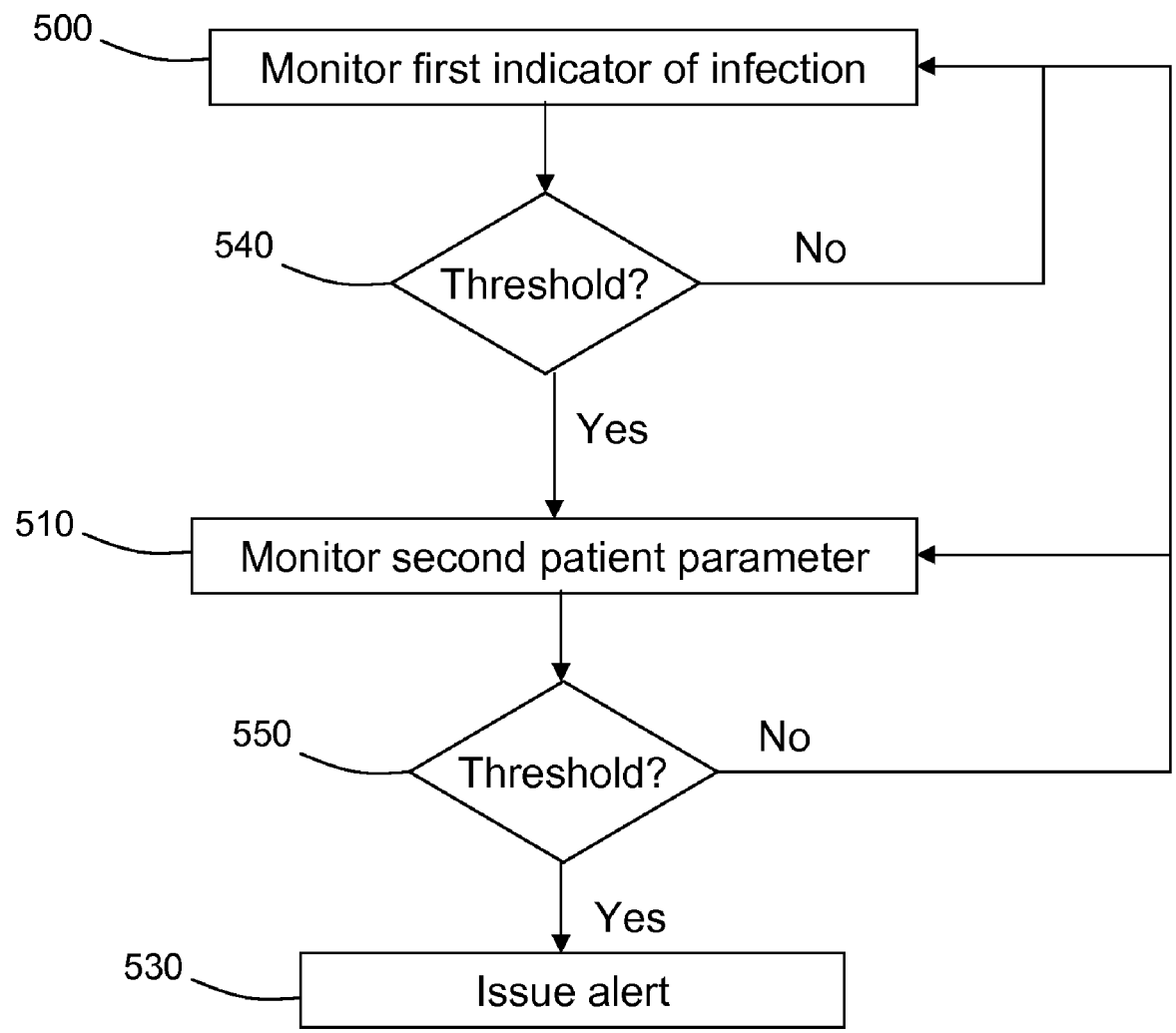

Referring to FIG. 11, an alternative method is shown. In FIG. 11, a first indicator of infection is monitored (500) and a determination is made as to whether a value associated with the monitored first indicator has crossed a threshold (540). If the value has crossed the threshold, monitoring of a second patient parameter may be commenced (510). Alternatively, the second patient parameter may be monitored in discrete time intervals and the frequency with which the second patient parameter is monitored may be increased if the value has crossed the threshold. A determination may be made as to whether a value associated with the monitored second parameter crosses a threshold (550) (or does not cross a threshold— e.g., as in FIG. 9B), an alert may be issued (530). If the value associated with the monitored second parameter does not (or does) cross a threshold, the process of monitoring the second patient parameter (510) and determining whether a value associated with the second patient parameter crosses a threshold (550) may be continued or the process of monitoring a first indicator of infection (500), determining whether a value associated with the first indicator crosses a threshold (540), monitoring the second patient parameter (510) and determining whether a value associated with the second patient parameter crosses a threshold (550) may be continued.

The method depicted in FIG. 11 may be desirable for implanted active devices 1, as power consumption may be conserved. That is, power that may otherwise be used for providing therapy is not diverted to monitoring the second patient parameter (510) until such information may be needed. Another way that power may be conserve is to monitor the first indicator of infection (500) in discrete time intervals rather than continuously, make determinations 520, 540, 550 in discrete time intervals, or the like. Additional information regarding reduction of power consumption while monitoring infection is described in US patent application Ser. No. 11/737,169, entitled "Event Triggered Infection Monitoring" naming Martin Gerber and John Rondoni as inventors, and U.S. patent application Ser. No. 11/737,170, entitled "Infection Monitorin", naming Martin Gerber and John Rondoni as inventors. The above-referenced patent applications are hereby incorporated herein by reference in their respective entireties to the extent that they do not conflict with the disclosure presented herein.

While not shown in FIGS. 7, 9-11, a step of implanting device 1 may be included in the methods described herein.

Thresholds values, against which values associated with monitored indicators or parameters may be compared, will be apparent to skilled practioners or readily obtainable through routine experimentation. Additional information regarding use of thresholds determining infection in proximity to an implantable medical device is provided in US patent application Ser. No. 11/737,180, entitled "Indicator Metrics For Infection Monitoring", filed on even date herewith, naming Martin Gerber and John Rondoni as inventors, which application is hereby incorporated herein by reference in its entirety to the extent it does not conflict with the disclosure presented herein.

By way of example, Table 1 provides some representative example thresholds that may be used according to the methods described herein.

TABLE 1

Reresentative Threshold Values for Representative Indicators and Parameters

| Parameter | Threshold | Threshold |
|---|---|---|
| Temperature* | >101° F. (38.3 C.) | >100.5° F. (38.1 C.) for two hours or more |
| pH* | <6.5, >7.5 | >10% deviation |
| Biological marker* | Presence of *S. aureus* antigen | IFN-γ 30% over average |
| Heart rate | >90 beats/min. | >50% above average |
| Footfalls | >50 footfalls/minute | >30% above average |

*Indicator of infection, detection in proximity to device

While merely for purposes of example, the thresholds provided in Table 1 will be discussed in greater detail. For example, a threshold 540, 550 may be crossed if a temperature of 101° F. (38.3 C) or greater is detected in proximity to device 1. Alternatively, or in addition, a threshold 540, 550 may be crossed if a temperature of 100.5° F. (38.1 C) or greater is detected for two hours or more. Other thresholds may include detection of pH in proximity to device 1 of less than 6.5 or greater than 7.5. Alternatively, or in addition, a threshold may include detection of a 10% or greater change in pH from a mean or median value determined over time. Other examples of suitable thresholds include detection of an *S. aureus* antigen in proximity to device 1 or a 30% or greater increase in IFN-γ relative to a mean or median value. Examples of thresholds associated with parameters associated with patient activity include heart rate and foot falls. Thresholds for heart rate may include 90 beats per minute or more or an increase of 50% or greater over a mean or median value. For footfalls, footfalls per minute or deviations from a median of mean value may be used to set or determine thresholds. Where not specifically indicated, it will be understood that the thresholds discussed with regard to Table 1 may, in some circumstances, be crossed with detection of a value, e.g. 200, 210, at a point in time or, in some circumstances, may be crossed with detection of a value over a period of time. Of course trends, other than those discussed above, in information regarding indicators of infection or second patient parameters may be used advantageously to improve the accuracy of determinations of infections in proximity to an implanted medical device.

As discussed herein, the accuracy of determinations of infections in proximity to an implanted medical device may be improved by using information regarding two or more indicators of infection or associated patient parameters. Suitable combinations of indicators of infection or indicators of infection an associated parameters will be apparent to skilled practitioners or readily obtainable through routine experimentation. Some representative examples of suitable combinations include (i) two or two or more indicators of infection and (ii) an indicator of infection and an associated patient parameter. Examples of pairs of indicators of infection that may be used include temperature and pH, temperature and impedance, temperature and a biological marker of infection, pH and impedance, pH and a biological marker of infection, and impedance and a biological marker of infection. Examples of pairs of an indicator of infection and an associated patient parameter include (i) temperature and a parameter related to patient activity, such as footfalls, movement, heart rate, and respiration rate; and (ii) pH and and a parameter related to patient activity. A determination may be made that an infection is in proximity to device 1 (520) and an alert may be issued (530) if temperature in proximity to the device is greater than 100.5° F. (38.1 C) for two hours or more during a period of time in which heart rate does not exceed 90 beats per minute for more than 30 minutes.

Figure 12A:
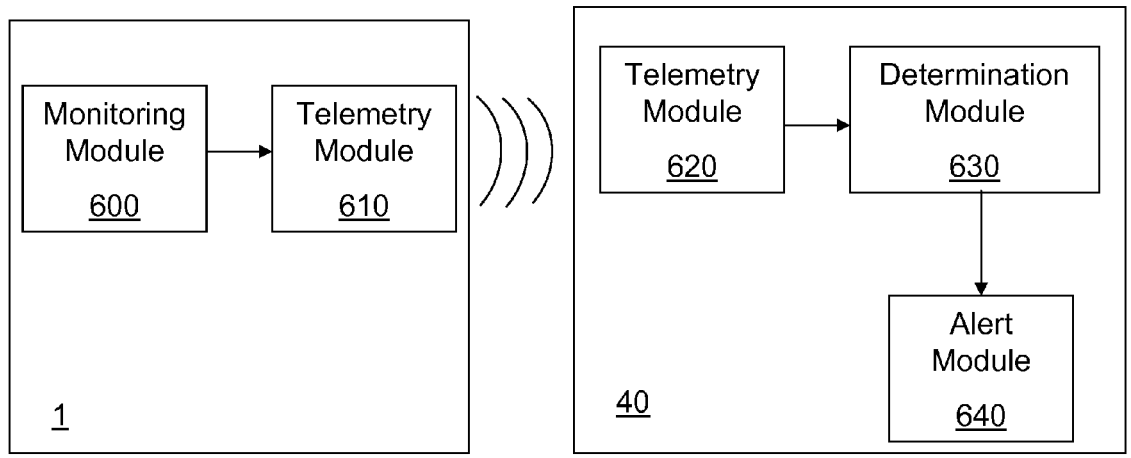
FIGS. 12A-D are schematic block diagrams of a representative implantable medical devices or systems.
Figure 12B:
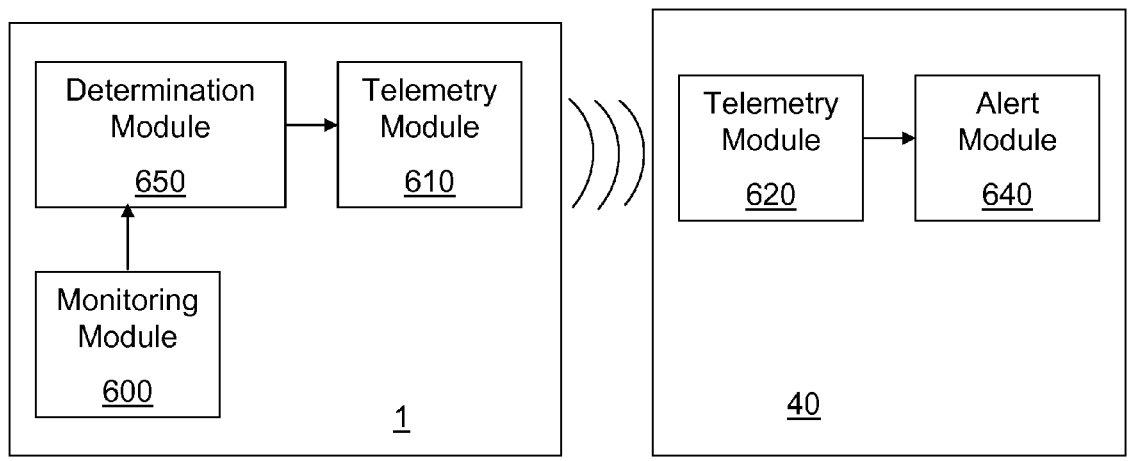
Figure 12C:
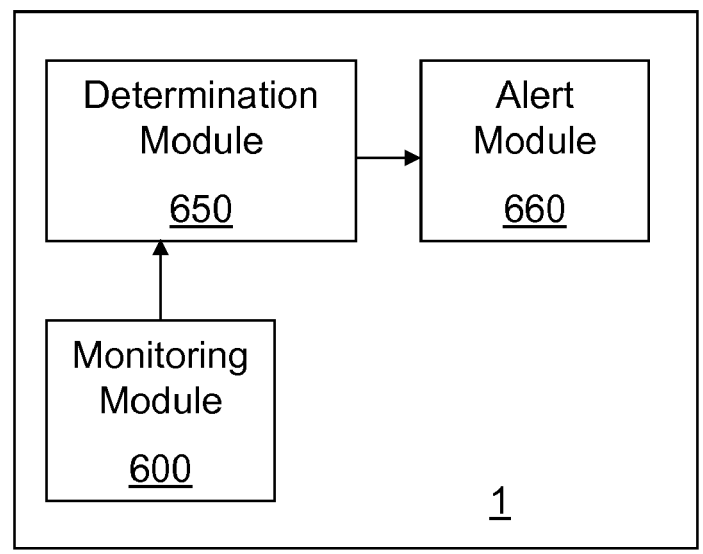
Figure 12D:
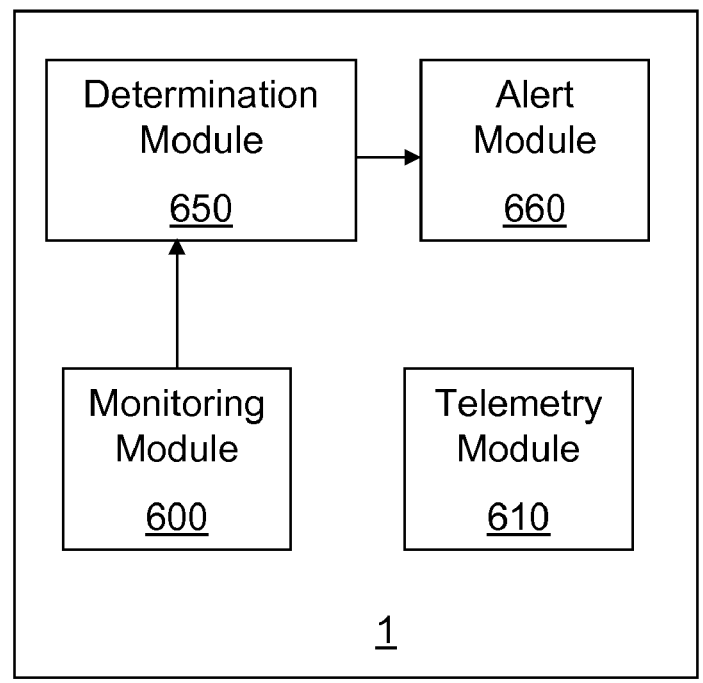

FIGS. 12A-D are block diagrams of representative devices or systems. It will be understood that one or more components described with regard to FIG. 6 may be included or carry out a function of one or more modules described in FIGS. 11A-D. As shown in FIGS. 11A-D, a system or device suitable for carrying out one or more method as discussed with regard to FIGS. 7, 9-11 may include one or more monitoring module 600, telemetry modules 610, 620, a determination module 630, and an alert module 640. Monitoring module 600 includes sensor 50 and allows for sensed information to be provided to device 1 and may be saved in memory 120. Determination module 630 includes processor 110 that may determine, based on sensed information, whether an infection in proximity to device 1 is likely. If an infection is likely, alert module 640 may be used to issue an alert, e.g. prompting the patient to seek appropriate medical attention. Telemetry modules 610, 620 may be used to communicate information from implanted device 1 to external device 40 (or from external device 40 to internal device 1). As shown in FIGS. 12A-B, certain modules or portions thereof may be in implanted device 1 and certain modules or portions thereof may be in external device 40. As shown in FIGS. 12 C-D, implanted device 1 may include sufficient components to carry out the methods described herein, whether or not device 1 includes a telemetry module 610 for communicating with external device 40.

One of skill in the art will understand that components or steps described herein regarding a given embodiment or set of embodiments may readily be omitted, substituted, or added from, with, or to components or steps of other embodiments or sets of embodiments, as appropriate or desirable.

It will be further understood that a computer readable medium containing instructions that when implemented cause an implantable medical device (or system including an implantable medical device) to perform the methods described herein are contemplated. In an embodiment the computer readable medium contains instructions that when implemented cause an implantable medical device to (i) monitor a first indicator of infection in proximity to the medical device implanted in a patient; (ii) monitor a second patient parameter; and (iii) determine whether the combination of the first indicator and the second parameter are indicative if infection in proximity to the implanted device. In various embodiments, the instructions, in causing the device to determine whether the first indicator and second parameter are indicative of infections, cause the device to determine whether a first value associated with the first indicator crosses a first threshold and determine whether a second value associated with the second patient parameter crosses a second threshold. The computer readable medium may further include instructions that when implemented cause the implantable medical device to determine whether a first value associated with the first indicator crosses a first threshold and increase the frequency of monitoring of the second patient parameter if the first valve crosses the first threshold. Devices including the computer readable medium are also contemplated.

In addition, the principles of the methods, systems and devices described herein may be used for detecting various other potential adverse health issues associated with an implantable medical device. For example, temperature, pH, impedance, and various indicators of infection may also be used to determine whether a hematoma, edema, or seroma is present in proximity to an implanted device. Accordingly, monitoring of such other potential adverse health issues is within the scope of the present disclosure.

Patent applications directed to infection monitoring that may provide additional insight into the teachings provided herein include the following patent applications filed on even date herewith:

(i) U.S. patent application Ser. No. 11/737,173, entitled "Infection Monitoring", naming Martin Gerber and John Rondoni as inventors; and (ii) US patent. application Ser. No. 11/737,179,entitled "Controlling Temperature During Recharge for Treatment of Condition", naming Martin Gerber and John Rondoni as inventors. The above-referenced patent applications are hereby incorporated herein by reference in their respective entireties to the extent that they do not conflict with the disclosure presented herein. Thus, embodiments of MULTI-PARAMETER INFECTION MONITORING are disclosed. One skilled in the art will appreciate that the present invention can be practiced with embodiments other than those disclosed. The disclosed embodiments are presented for purpose of illustration and not limitation, and the present invention is limited only by the claims that follow.

What is claimed is:

1. A method comprising:
   monitoring, via an implantable medical device, a first indicator of infection in proximity to the medical device implanted in a patient;
   monitoring a second patient parameter that provides information regarding whether the first indicator is indicative of infection, wherein the second patient parameter is not an indicator of infection; and
   determining whether the combination of the first indicator and the second parameter are indicative of infection in proximity to the implanted device,
   wherein determining whether the combination of the first indicator and second parameter are indicative of infection in proximity to the implanted device comprises:
      determining whether a first value associated with the first indicator crosses a first threshold; and
      determining whether a second value associated with the second patient parameter crosses a second threshold,
      wherein the combination is determined to be indicative of infection if the first value crosses the first threshold and the second value does not cross the second threshold.

2. The method of claim 1, further comprising issuing an alert if the combination of the first indicator and the second parameter are indicative of infection in proximity to the implanted device.

3. The method of claim 1, wherein monitoring the second patient parameter comprises monitoring a parameter related to patient activity.

4. The method of claim 3, wherein monitoring a parameter related to patient activity comprises monitoring heart rate.

5. The method of claim 3, wherein monitoring the first indicator of infection comprises monitoring temperature.

6. The method of claim 1, further comprising determining whether a value associated with the first indicator of infection crosses a threshold, wherein monitoring the second patient parameter commences when the value associated with the first indicator of infection crosses the threshold.

7. The method of claim 1, wherein monitoring the second patient parameter comprises monitoring the second parameter in discrete time intervals.

8. The method of claim 7, further comprising determining whether a value associated with the first indicator of infection crosses a threshold, wherein the frequency with which the second parameter is monitored is increased if the value associated with the first indicator crosses the threshold.

9. A computer readable medium comprising instructions that when implemented cause an implantable medical device to:
   monitor a first indicator of infection in proximity to the medical device implanted in a patient;
   monitor a second patient parameter that provides information regarding whether the first indicator is indicative of infection, wherein the second patient parameter is not an indicator of infection; and
   determine whether the combination of the first indicator and the second parameter are indicative if infection in proximity to the implanted devices,
   wherein the determination of whether the combination of the first indicator and second parameter are indicative of infection in proximity to the implanted device comprises:
      determining whether a first value associated with the first indicator crosses a first threshold; and
      determining whether a second value associated with the second patient parameter crosses a second threshold,
      wherein the combination is determined to be indicative of infection if the first value crosses the first threshold and the second value does not cross the second threshold.

10. The computer readable medium of claim 8, further comprising instructions that when implemented cause the implantable medical device to:
   determine whether a first value associated with the first indicator crosses a first threshold; and
   increase the frequency of monitoring of the second patient parameter if the first valve crosses the first threshold.

11. An implantable medical device comprising:
   the computer-readable media of claim 9;
   electronics capable of executing instructions of the computer readable medium;
   a first sensor capable of detecting the first indicator of infection and providing the electronics with information regarding the first indicator; and
   a second sensor capable of detecting the second patient parameter and providing the electronics with information regarding the second parameter.

12. An implantable medical device comprising:
   the computer-readable media of claim 10;
   electronics capable of executing instructions of the computer readable medium;
   a first sensor capable of detecting the first indicator of infection and providing the electronics with information regarding the first indicator; and
   a second sensor capable of detecting the second patient parameter and providing the electronics with information regarding the second parameter.

* * * * *